United States Patent [19]

Blay

[11] 4,008,279
[45] Feb. 15, 1977

[54] PROCESS FOR DEHALOGENATION AND/OR PREVENTION OF HALOGENATION

[75] Inventor: Jorge A. Blay, Corpus Christi, Tex.

[73] Assignee: Celanese Corporation, New York, N.Y.

[22] Filed: Aug. 15, 1974

[21] Appl. No.: 497,609

[52] U.S. Cl. .................. 260/601 R; 260/601 H
[51] Int. Cl.² .................. C07C 47/06; C07C 47/14
[58] Field of Search ................ 260/601 H, 601 R

[56] References Cited

UNITED STATES PATENTS 3,149,167  9/1964  Hornig et al. ............... 260/604 AC

FOREIGN PATENTS OR APPLICATIONS 750,422  1/1967  Canada ..................... 260/604 AC
930,143  7/1963  United Kingdom ......... 260/604 AC

*Primary Examiner*—James O. Thomas, Jr.
*Assistant Examiner*—W. B. Lone
*Attorney, Agent, or Firm*—Stewart N. Rice; Ralph M. Pritchett

[57] ABSTRACT

A process for dehalogenation of alpha halogenated carbonyl compounds and/or the prevention of the formation of such. The process for dehalogenation generally comprises causing there to be in solution the halogenated compound, cuprous ions (such as from cuprous chloride) and hydrogen ions (such as from hydrochloric acid), the process to be conducted in the absence of molecular oxygen, or, if molecular oxygen is present, there being an excess of cuprous ions sufficient to completely react with the molecular oxygen present. Such can also be used to suppress formation of halogenated carbonyl compounds in processes where conditions exist which favor such formation.

4 Claims, 2 Drawing Figures

PROCESS FOR DEHALOGENATION AND/OR PREVENTION OF HALOGENATION

BACKGROUND OF THE INVENTION

The present invention relates to a method for the dehalogenation of an alpha halogenated carbonyl compound or in some instances to the prevention of the formation of such alpha halogenated carbonyls from the corresponding non-halogenated carbonyls. The word "dehalogenation" as used herein is meant to include both complete dehalogenation as well as a mere reduction in the degree of halogenation. Further, "dehalogenation" as used herein involves the replacement of the halogen ions with hydrogen ions, and does not include dehydrohalogenation.

There are many instances wherein it may be desirable to dehalogenate an alpha halogenated carbonyl compound, that is to replace the alpha halogen atoms with hydrogen atoms. In some instances where there is more than one alpha halogen atom present, the dehalogenation desired may merely be from a high degree of halogenation to a lower degree of halogenation, such as the dehalogenation of a tri-halogenated aldehyde to form a di-halogenated aldehyde; or it may be desired to effect complete dehalogenation such as the conversion of a tri-halogenated aldehyde to the corresponding non-halogenated aldehyde. The desire to effect the dehalogenation may sometimes arise because the halogenated carbonyl compound is an undesirable by-product of a chemical process, in which instance the same net results may usually be accomplished by merely suppressing the formation of the halogenated carbonyl.

For example, there is a well known conversion process for the conversion of an alkene to an aldehyde (such as ethylene to acetaldehyde) wherein in a first stage the alkene is reacted with an aqueous acidic solution of an oxidant catalyst system comprising a noble metal together with a redox agent comprising cupric chloride, the aldehyde then being separated from the spent catalyst solution which is in a chemically reduced form. The spent catalyst solution is then reoxidized with a source of molecular oxygen (typically air) before being recycled to the first stage of the process for the conversion of additional quantities of alkene. Such a process is described, for example, in a paper by Dr. J. Smidt in "Chemistry And Industry" (Jan. 13, 1962), pages 54–61. In such conversion process, a continuing problem has been that in addition to the production of the desired non-halogenated aldehyde product, there is also produced minor amounts of chloroaldehydes. These chloroaldehydes represent a product loss and therefore a satisfactory method for dehalogenating them to the desired non-halogenated aldehyde is desired so as to improve the overall yield. Further, from an ecological standpoint the dehalogenation of these chloroaldehydes is desirable since disposal of halogenated compounds presents environmental problems.

The foregoing is just one example of an industrial process where the dehalogenation of a halogenated carbonyl compound is desired although there are numerous other situations where such is obviously desirable. It is thus an object of the present invention to provide a process for the dehalogenation of alpha halogenated compounds, including complete dehalogenation of the alpha halogens, as well as, when treating a halogenated carbonyl compound having more than one alpha halogen, the replacement with hydrogen of less than all the alpha halogens. It is a particular object of the present invention to provide a process for the dehalogenation of the chlorinated acetaldehydes. From the description of the foregoing alkene conversion process, it may be recognized that the necessity for dehalogenation in that particular process is brought about by an undesirable halogenation, and thus in such particular process the same net result, that is production of a non-halogenated aldehyde product free of contamination by halogenated derivatives, could be accomplished by the prevention of the halogenation in the first instance. The inventor's discovery disclosed herein allows such to be accomplished and the accomplishment of such is an additional object of the invention.

SUMMARY OF THE INVENTION

Figure 1:
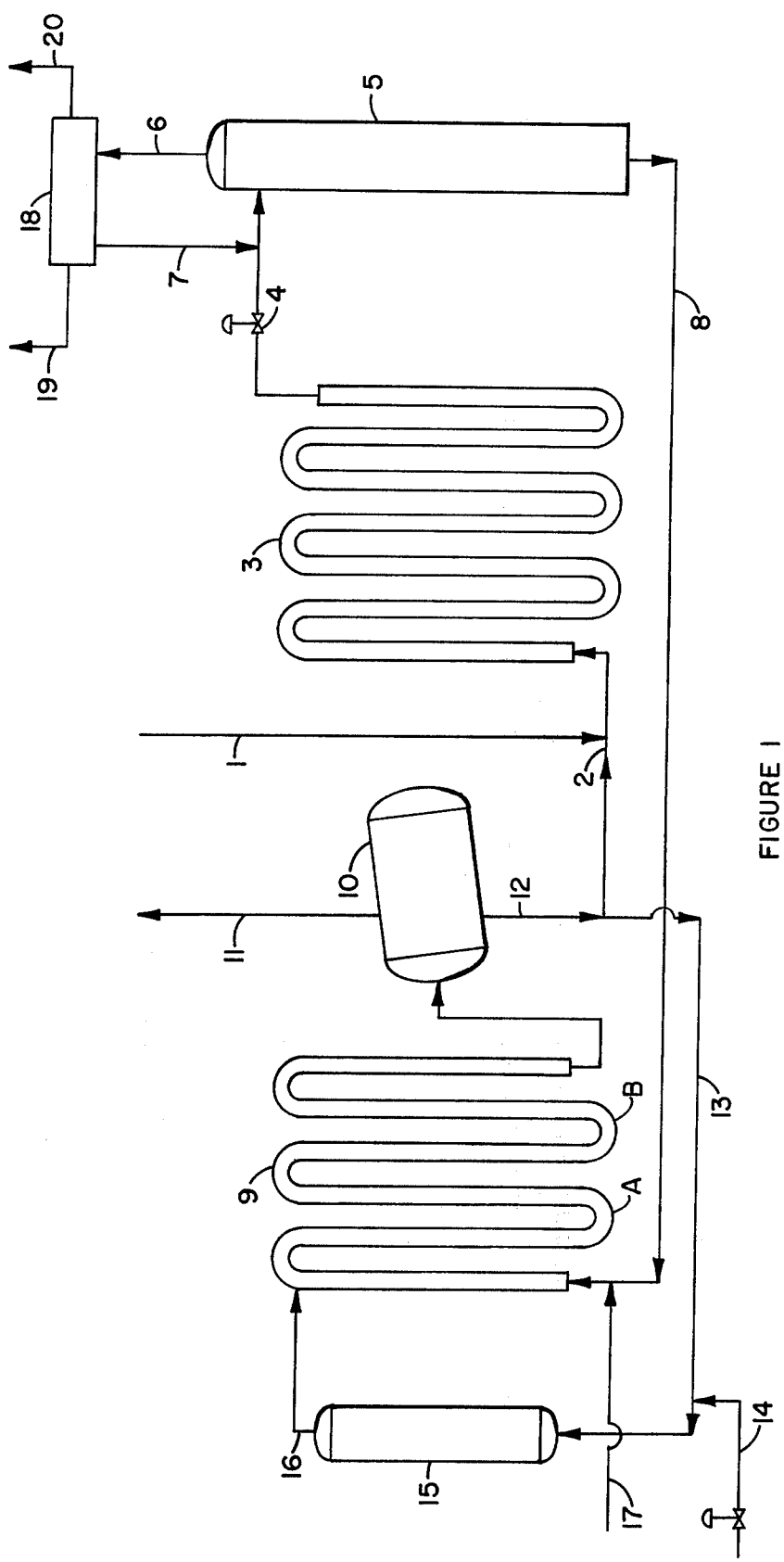
FIG. 1 is a simplified schematic flow sheet of an alkene conversion process wherein an alkene may be converted to an aldehyde.

The foregoing objects and additional objects are accomplished by the present invention which in one of its aspects is a process for replacing an alpha halogen atom on an alpha halogenated carbonyl compound with a hydrogen atom, said process comprising causing there to be in solution of said halogenated carbonyl compound at least one hydrogen ion in solution for each halogen ion to be so replaced, and at least sufficient cuprous ions in solution to completely react with and be oxidized by any molecular oxygen present, plus at least two cuprous ions for each halogen ion to be replaced. In another of its aspects the present invention is an improvement in a continuous conversion process for converting an alkene to an aldehydo alkane product by (a) passing said alkene through an alkene reaction zone concurrently with an acidic oxidant catalyst solution comprising a liquid containing a noble metal oxidation catalyst, cupric ions, and chloride ions, whereby said alkene is oxidized to form a reaction product comprising predominantly said aldehydo alkane product admixed with said catalyst solution in a chemically reduced condition; (b) separating said reaction product into fractions comprising (i) an aldehydo alkane product fraction and (ii) a reduced catalyst solution fraction containing said noble metal and copper in a reduced form, including cuprous chloride in solution and as cuprous chloride crystals, and also containing hydrochloric acid, and also containing amounts of said aldehydo alkane as well as alpha chlorinated aldehydo alkane; (c) in a catalyst reoxidation zone reoxidizing said reduced catalyst solution with a gas comprising molecular oxygen to oxidize a portion of the copper values contained therein to the cupric form; and (d) recycling the resulting reoxidized catalyst solution to said alkene reaction zone; which improvement comprises adding said gas comprising molecular oxygen to said catalyst reoxidation zone in a plurality of increments.

DETAILED DESCRIPTION OF THE INVENTION

It is known that carbonyl compounds can be alpha halogenated by the reaction in solution with cupric chloride, for example:

$$CH_3CHO + 2CuCl_2 \rightarrow CH_2ClCHO + 2CuCl + HCl \qquad (I)$$

It is now been discovered that the above reaction may be reversed if conducted in the absence of molecular oxygen. Further the reaction may be reversed even in the presence of molecular oxygen if there are sufficient cuprous ions present in solution (1) to completely react with and be oxidized to cupric ions by any such molecular oxygen present, and (2) the stoichemetric amount of cuprous ions necessary in the dehalogenation, that is two cuprous ions per halogen atom to be replaced. It is emphasized that the cuprous ions must be in solution (as opposed to being present in the form of cyrstals, such as cuprous chloride crystals) in order to react with any molecular oxygen present. Thus the following reaction may be made to occur:

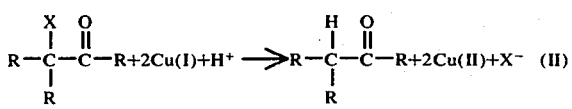

Cu(I) being a cuprous ion, Cu(II) being a cupric ion, R being hydrogen or an organic radical, and X being a halogen atom in such Reaction II, or, as a specific example:

$$CH_2ClCHO + 2CuCl + HCl \rightarrow CH_3CHO + 2CuCl_2 \qquad (III)$$

The discovery disclosed herein also may be used to advantage in a situation where an alpha halogenation (such as in Reaction I above) occurs but is undesired, that is the discovery disclosed herein may be used to hinder an alpha halogenation of a carbonyl compound. The hindrance of the halogenation of a carbonyl compound in accordance with Reaction I above can be effected by causing there to be sufficient cuprous ions in solution to completely react with any molecular oxygen which is present in the system, it appearing that the presence of molecular oxygen is necessary in order to effect Reaction I above. To the inventor's knowledge such required presence of molecular oxygen was not known prior to his discovery thereof. Such discovery can be used to beneficial effect in the above mentioned alkene conversion process where, as such alkene conversion process has heretofore been conducted, conditions in the catalyst reoxidation zone have existed which favor the halogenation pursuant to Reaction I above.

The present invention is applicable to the various alpha halogenated carbonyl compounds, the term "carbonyl compound" meaning one containing a carbonyl group so as to include the organic ketones, aldehydes and carboxylic acids. Most generally the alpha halogenated carbonyl compounds will be the acyclic or carbocyclic carbonyl compounds which are free of ethylenic or acetylenic unsaturation between the carbonyl group and the alpha carbon on which the halogen to be replaced is located. Structurally, the alpha halogenated carbonyl compounds to which the present invention will most likely be applied may be represented by the following formula:

wherein in Formula IV above, $X_1$ is a halogen atom, $X_2$ is a hydrogen atom, a monovalent organic radical or a halogen atom, $X_3$ is a hydrogen atom, a halogen atom, a monovalent organic radical or a divalent organic radical, and $R_1$ is hydrogen, a hydroxyl group, a monovalent organic radical or a divalent organic radical, and when $X_3$ and $R_1$ are divalent organic radicals such being joined to each other as indicated by the dashed line so as to compositely form a cyclic compound. Where $X_2$, $X_3$ and/or $R_1$ are organic radicals, they most generally will be the substituted or unsubstituted hydrocarbon radicals free of acetylenic unsaturation, containing no hetero or etheral oxygens and free of substituents other than carbonyl groups, halogen atoms, and carboxylic acid groups or alkyl salts thereof. The alpha halogenated carbonyl compounds will generally contain from about 2 to 20 carbon atoms.

The present invention is especially useful in treating those acyclic aldehydes, ketones and carboxylic acids corresponding to Formula IV above (with the dashed line removed), preferably of 2 to 10 carbon atoms, wherein $X_1$ is halogen, $X_2$ and $X_3$ are halogen, hydrogen or alkyl groups, and $R_1$ is hydrogen, a hydroxyl group, an alkyl group or a haloalkyl group, with the invention being especially suited for treating the aldehydes wherein $R_1$ is a hydrogen atom. The especially preferred carbonyl compounds for dehalogenating in accordance with the present invention are those aldehydo alkanes of 2 to 6 carbon atoms wherein, in Formula IV above (with the dashed line removed), $X_1$ is a halogen atom, $X_2$ is a halogen atom or a hydrogen atom and $X_3$ is a halogen atom, hydrogen atom or an alkyl group. Some specific halogenated carbonyl compounds containing alpha halogen atoms which may be replaced with hydrogen atoms in accordance with the present invention include 2,2,3-trichlorobutanal; 2-chloropentanal; monochloroacetaldehyde; tribromoacetaldehyde (bromal); trichloroacetaldehyde (chloral); dichloroacetaldehyde; 2-chloro-2-methylpropanal; 2-bromo-3-methylbutanal; trialphachlorobutyric acid; monoalphachloroacetic acid; 2-bromobutyracetal; dialphabromobutyric acid; chloromethyl cyclopropyl ketone; dichloromethyl cyclopropyl ketone; 3-chloro-3-buten-2-one; 6-chloro-3,5,5-trimethyl-2-cyclohexenone; 2-bromo-5,5-dimethylcyclohexnene-1,3-dione; 2-bromoorthohydroxyacetophenone; 6-(bromoacetyl)-5-dimethyl-cyclohexene-4-methylcoumarin; 8-(bromoacetyl)-7-hydroxy-4-methylcoumarin; 3 betahydroxy-16 alpha-bromo-5 alpha-androstan-17-one; and 2-chlorohexanoic acid. Where there are halogen atoms present on the carbonyl compound at other than the alpha position, such halogen atoms will not be removed (replaced) in accordance with the present invention.

The alpha halogen atoms that may be replaced with hydrogen may be any of the halogens, that is fluorine, chlorine, bromine and iodine, and the present invention is effective where two or more different halogens are in the alpha position, for example 1-bromo-1-chloroacetaldehyde. The halogens most susceptible to replacement with hydrogen in accordance with the present invention are chlorine and bromine, especially chlorine.

In conducting the dehalogenation process a wide variety of conditions of temperature and pressure may be utilized. Generally speaking the temperature should be within the range of about 70° to 250° C with temperatures within the range of 110° to 180° C preferred. Since the reaction is to be conducted in the liquid phase, the pressure required will vary according to the temperature at which the reaction is conducted, the main requirement being that the pressure be sufficient to maintain a liquid phase. For the temperatures under which the dehalogenation reaction may be conducted, the minimum pressure required may thus vary from as low as 5 p.s.i.g. up to 600 p.s.i.g. The maximum pressure may greatly exceed that required to maintain a liquid phase without adversely affecting the process and may for example be as high as 2,000 psig and higher. Thus, generally speaking the pressure at which the reaction may be conducted will be within the range of 5 to 2,000 psig.

Of critical importance in the present invention is the presence in solution of cuprous ions. Generally such may be derived from a cuprous salt of a strong acid, cuprous chloride being a preferred source of the cuprous ions. Other salts including salts of carboxylic acids, may however be utilized, such as cuprous bromide, cuprous fluoride, cuprous iodide, cuprous sulfate, cuprous sulfite, cuprous acetate, cuprous propionate, and the like. The cuprous ions could also be derived from such compounds as cuprous oxide. Preferably the cuprous ion is derived from a salt, the anion of which is the same as that of the acid used as a source of the hydrogen ions, and, more preferably, the cuprous ion is derived from a cuprous halide, the halide portion of which corresponds to the alpha halogen atom being removed from the alpha halogenated aldehyde, with the acid being a halogen acid corresponding to the cuprous halide. By having the anion derived from the cuprous salt and the anion derived from the acid the same as the alpha halogen atom being removed, mixtures of anions in the reaction product are prevented such that separation of the reaction product into its various components is more easily effected.

From the foregoing Reaction II, it may be seen that the stoichemetric amount of cuprous ions required for effecting a dehalogenation is two cuprous ions per alpha halogen atom to be replaced with a hydrogen atom. Further, since Reaction II does not take into account any molecular oxygen which may be present, there must also be sufficient cuprous ions to completely react with such oxygen. Upon so reacting with the oxygen the cuprous ions are oxidized to cupric ions, the stoichemetric amount of cuprous ions required being four atoms per molecule (or four equivalents per mole) of molecular oxygen. Where the discovery disclosed herein is used merely to suppress formation of alpha halogenated aldehydes, there is required only the amount of cuprous ions in solution necessary to completely react with any molecular oxygen, and, the stoichemetric amount required for Reaction II is not needed. This point will be discussed in more detail below in relation to the alkene conversion process. The following illustrates the oxidation of cuprous ions to cupric ions in a situation where cuprous chloride is the source of the cuprous ions and hydrochloric acid is the source of the hydrogen ions:

$$4CuCl + 4HCl + O_2 \rightarrow 4CuCl_2 + 2H_2O \quad (V)$$

The exact amount of cuprous ions required to be in solution will thus vary according to the concentration of the alpha halogenated aldehyde to be dehalogenated and will be limited also by the solubility of the source of the cuprous ions. Where there is a saturated solution of cuprous ions with crystals of a cuprous salt present, the salt will dissolve to provide more cuprous ions in solution as the cuprous ions in solution are oxidized to cupric ions. There is some finite time lag in such a situation between the time that a cuprous ion is oxidized and the time that a cuprous salt crystal dissolved so as to again saturate the solution with respect to cuprous ions. This time lag is of special importance in applying the discovery herein disclosed to the foregoing alkene conversion process. When a choice of reaction conditions can be selected it is preferable to treat a solution of the alpha halogenated carbonyl compound which is from about 0.05 to 1.0 molar in such carbonyl compound. This is not to say that lesser or greater amounts are inoperable, and, in fact in the alkene conversion process described herein there will be very small amounts of the alpha halogenated aldehyde present, if any.

The amount of hydrogen ions needed in solution may also be determined from Reactions II and V above, there being required at least four hydrogen ions for each molecule of oxygen (according to Reaction V) and at least one hydrogen ion for each halogen ion to be replaced according to Reaction II. The required amount of hydrogen ions can generally be satisfied by maintaining the pH of the reactants within the range of about −1.0 to 3.0, preferably about 0.1 to 2.0.

In order to more fully describe the possible application of the discovery disclosed herein to the foregoing alkene conversion process, reference is made to FIG. 1. The process as represented in FIG. 1 and as described immediately hereafter illustrates the alkene conversion process as such has been heretofore operated without the benefit of the discovery disclosed herein. Further, in the following description ethylene will be employed as the alkene being processed, with acetaldehyde being the reaction product, but as previously explained it will be understood that other alkenes, especially lower alkenes having up to, for example, about 6 carbon atoms are also oxidized to produce corresponding aldehyde derivatives.

An oxidant catalyst solution comprising an aqueous solution of palladous chloride, cupric chloride, and hydrochloric acid, which is drawn from separator 10 through conduit 2, is mixed with ethylene introduced through conduit 1 and the resulting mixture is passed through alkene reaction zone or alkene oxidation reaction 3 at a temperature of about 110° C and under a pressure of about 11 atmospheres absolute. The catalyst solution comprises approximately 6 millimoles per liter of palladous chloride, 1000 millimoles per liter of cupric chloride, 100 millimoles per liter of cuprous chloride, 8 weight percent of acetic acid, and the remainder water. Small quantities of organic reaction by-products may also be present to the extent that these have passed through the product recovery and catalyst regeneration systems which will be described.

In the alkene oxidation reactor the ethylene is oxidized to acetaldehyde at nearly 100% conversion per pass, while simultaneously at least a portion of the cupric chloride, which acts as a redox agent in conjunction with the palladous chloride catalyst, is chemically reduced to cuprous chloride. Thus the product discharged from the alkene oxidation reactor is an aqueous solution containing hydrochloric acid, copper chlorides, and palladium moiety which may be present as the chloride, as Pd°, or as a mixture of the two. Also present will be a quantity of gases comprising any unreacted ethylene as well as any fixed gases which are formed in the reaction. Also present are small quantities of dissolved reaction by-products such as chloroacetaldehydes, oxalate ions, etc.

The reaction product just described is discharged through throttle valve 4, which acts to maintain a constant back-pressure at a point at or near the discharge end of the reactor. Throttle valve 4 discharges into stripping tower 5, in which acetaldehyde and other volatile reaction products are stripped from the catalyst solution along with any fixed gases, such as ethylene, which are present.

The stripped-out volatile materials pass from the stripping tower through conduit 6 into product recovery and purification system 18, which is shown in the drawing as a simple rectangle for the sake of simplicity although it will be recognized that this in actual fact is a complicated system of distillation towers, etc. in which the crude product mixture is separated into acetaldehyde product (withdrawn through conduit 20), a vent gas stream (discharged through conduit 19), and recycled water (returned to the stripping tower through conduit 7 along with such fresh water as may be needed to maintain a constant inventory of water in the reaction system). It will be recognized also that volatile reaction by-products, e.g. chlorinated organic compounds including the chlorinated acetaldehydes, also enter the product recovery system through conduit 6 and are ultimately separated from the acetaldehyde.

Stripping tower 5 acts, as has been explained, to remove volatile and gaseous materials from the reactor product discharged from reactor 3. It operates at a constant pressure of approximately 1.5 atmospheres absolute when the process is being employed to convert ethylene to acetaldehyde. The stripped catalyst solution drawn from the base of the stripping tower through conduit 8 comprises mainly an aqueous solution of hydrochloric acid, palladium moiety, cupric and cuprous chlorides, and non-volatile reaction by-products such as oxalates and non-volatile chlorinated organic compounds, and also generally contains small amounts of acetaldehyde and in some instances chlorinated acetaldehydes. The stripped catalyst solution will generally be saturated with respect to cuprous chloride such that the cuprous chloride is present in solution as well as in crystalline form. This chemically reduced depleted catalyst solution is mixed with air or other equivalent source of molecular oxygen through conduit 17 and passed through catalyst reoxidation reactor 9, within which cuprous chloride contained in the catalyst solution is reoxidized to the cupric form in the course of being passed cocurrently through the reactor 9 with the oxygen. Reactor 9 operates at approximately 12 atmospheres absolute and at a temperature of approximately 115° C, with sufficient oxygen being introduced to oxidize all the introduced cuprous salts to the cupric form.

The reoxidized catalyst solution discharged from reactor 9 enters gas-liquid separator (oxygen separator) 10, which is typically operated at a constant pressure of approximately 11 atmospheres absolute. Excess oxygen and any inert gases, e.g. nitrogen, which are present are discharged from separator 10 through conduit 11, while the reoxidized catalyst solution, now freed from gases, is drawn off through conduit 12.

The solution drawn from the separator through conduit 12 is split into a main stream, which is returned to the alkene-oxidation reactor through conduit 2, and a slip stream which is diverted to catalyst regenerator 15 through conduit 13, along with hydrochloric acid which is introduced at a controlled rate through conduit 14.

The regenerator 15 generally operates at approximately 160° C and 13 atmospheres absolute to decompose acid-decomposable reaction by-products, including specifically, the oxalate moiety, and to reincorporate sufficient hydrochloric acid into the catalyst solution to compensate for the chloride moiety withdrawn from the system through conduit 6 in the volatile reaction products stripped out of the alkeneoxidation reactor product. Acid-treated catalyst solution discharged from tthe regeneration reactor is returned to the reoxidation reactor 9 through conduit 16.

Both reoxidation reactor 9 and alkene-oxidation reactor 3 are elongated tubular reactors, each being composed of a series of vertically-oriented tubes connected with U-bends to form an elongated reaction path for the mixture of liquid and gas passing cocurrently therethrough. Typical liquid throughput in each of these reactors is of the order of 9 cubic feet per second per square foot of tube cross-section. Because of the extremely corrosive nature of the catalyst solution, the reactors, as well as other process apparatus exposed to the catalyst solution, are either fabricated of titanium or lined wih titanium.

In operation of the system just described, constant pressures are generally maintained in separator 10, at the discharge end of reactor 3, and in stripping column 5. The flow of liquids and gases through reactors 9 and 3 is also maintained at as constant a rate as is possible, and, as has been noted previously, the volume of catalyst solution within the over-all system is also maintained constant by replenishing water losses from the system through, for example, conduit 7.

From the foregoing description of the operation of the ethylene to acetaldehyde conversion process, and with the knowledge of the discovery herein disclosed, it will be recognized that conditions exist in the catalyst reoxidation reactor 19 which favor the alpha chlorination of the minor amounts of acetaldehyde which enter catalyst reoxidation ractor 9 through conduit 8 in accordance with Reaction I, and which conditions also prevent the dehalogenation of any chlorinated acetaldehydes which have entered catalyst reoxidation reactor 9. More specifically, as the alkene conversion process has heretofore been conducted, the entire amount of oxygen needed in the catalyst reoxidation has been introduced in relatively concentrated form (such as air or pure oxygen) at one time at the entrance to the catalyst reoxidation zone. Since it takes a finite time for the oxygen to oxidize the cuprous ions to cupric ions, the prior method of introducing the oxygen causes there to be present large excesses of molecular oxygen, the amount of molecular oxygen decreasing as the reactants move through the catalyst reoxidation reactor 9. One reason for the time period required for the molecular oxygen to completely react with and oxidize the cuprous ions is that all of the cuprous ions are not in solution at the beginning of the reoxidation reactor but are instead present as cuprous chloride crystals in equilibrium with a saturated solution of dissolved cuprous chloride. When molecular oxygen oxidizes a cuprous ion in solution to form a cupric ion, the solution then becomes unsaturated with cuprous chloride and allows more cuprous chloride crystals to dissolve so as to again saturate the solution, the thus dissolved cuprous ions then being oxidized by the molecular oxygen. The oxidation of cuprous ions in solution followed by dissolution of more cuprous chloride crystals goes on cyclicly until all of the molecular oxygen is depleted and/or all of the cuprous ions present are oxidized to cupric ions.

In order to take advantage of the discovery herein disclosed, the manner of addition of the oxygen to the catalyst reoxidation zone would preferably be controlled such that there was substantially always some finite amount of cuprous ions in solution. One way to accomplish this is by adding the molecular oxygen in increments such that the amount added in each increment is preferably not in excess of the amount required to oxidize the cuprous ions in solution at such time. After (1) an incremental amount of oxygen is added, (2) the oxygen has oxidized the cuprous ions, and (3) additional cuprous ions have been brought into solution by dissolution of cuprous chloride crystals, then another incremental amount of oxygen will be added, the amount of which is preferably not in excess of the amount required to oxidize the cuprous ions then in solution. The maximum amount of oxygen to be added can be determined from Reaction V above, that is only 1 mole of oxygen is needed for the oxidation of each 4 equivalents of cuprous chloride in solution. For any particular reactor, the amount of cuprous ions in solution at any given point along the length of the reactor may be determined in order to determine the optimum number of increments required for addition of the oxygen in accordance with the present invention. Instead of actually determining the amount of cuprous ions in solution at any given point along the reactor, a study may be made of the molecular oxygen content at any given point along the reactor in order to determine the rate at which oxygen is normally consumed. The total oxygen to be fed to the reactor can then be added in increments based on the amounts which may thus be consumed at any given point in the reactor.

The goal to be achieved is that at all times there will be a finite amount of cuprous ions present in solution, however those skilled in the art recognize that in an industrial application such may be impossible from a practical standpoint. However even if there is a finite amount of cuprous ions present only a substantial amount of the time, improved results will still be obtained; and, in fact, improved results will be obtained even if the oxygen is added in only two increments.

Another method of controlling the oxygen added to the catalyst reoxidation zone such that there is substantially always a finite amount of cuprous ions present is to dilute the oxygen to such an extent that the reoxidation rate is slowed. The diluent utilized should of course be an inert diluent, that is one which does not decompose or react with itself or with the other compounds and elements present under the temperatures and pressures involved. Preferably the inert diluent is one of the inert gases such as helium, neon or argon, with helium being preferred. Other diluents which are inert under the conditions which exist in the catalyst reoxidation zone and which may be utilized are nitrogen, carbon dioxide, methane and ethane. The amount of inert diluent utilized must be sufficient to depress the rate at which the oxygen oxidizes the cuprous ions in solution such that additional cuprous ions may be brought into solution (through the dissolution of the cuprous chloride crystals) prior to the oxidation of the cuprous ions present at any given time. This can generally be accomplished by diluting the oxygen concentration in the gas added as a source of oxygen to less than 20% by volume, preferably from about 2 to 10% by volume. The diluent may be mixed with the oxygen prior to addition to the catalyst reoxidation zone, which is preferred, or other methods may be used such as adding the oxygen and diluent separately to the catalyst reoxidation zone. The incremental addition of oxygen is preferred over the use of diluents, however in some instances a combination of the two methods may be utilized. Actually when using air as the source of oxygen, there are diluents naturally present but such are not present in sufficient amounts to slow the reaction rate to that desired in order to take advantage of the discoveries disclosed herein.

When operating using incremental addition of oxygen, the addition of the increments of oxygen may be continuous or intermittent. By the term "incremental addition of oxygen" and related terms is meant that the total amount of oxygen is not added to the catalyst reoxidation zone at one time and at one place. Thus in the plug-flow tubular reactor of a continuous process as shown in FIG. 1, the oxygen addition may indeed by continuous except that instead of one point of continuous addition at the beginning of the tubular reactor, there would be a plurality of points of continuous oxygen addition spaced along the length of the reactor. If a back mixed reactor were utilized instead of a plug-flow reactor, the incremental addition of oxygen would most likely be at the same point in the reactor but at spaced intervals of time. The number of increments used will depend somewhat on the physical size of the process equipment being used, residence time in the reactor, and the like. Generally, however, from about 2 to 10 increments will suffice, with from about 4 to 8 preferred. For safety reasons the incremental addition of oxygen should be such that the reactor effluent as a very low oxygen level out of the explosive range. This can be accomplished in a plug-flow reactor by adding the last increment well before the end of the reactor. Thus, for safety reasons there should generally be no increment added to a plug flow reactor near the effluent end than the length of the reactor divided by the number of increments.

The process of the present invention will generally be conducted in an aqueous solution however any solvent in which the halogenated carbonyl compound, the source of hydrogen ion and the cuprous chloride are soluble, and, which under reaction conditions does not decompose and is not reactive with itself or with the other reactants present to any appreciable extent. When the alpha halogenated carbonyl compound of concern is a carboxylic acid then the corresponding non-halogenated carboxylic acid will usually serve as an excellent solvent. Mixtures of water with a lower alkanol, such as methanol and ethanol, will serve as a solvent provided that there is present in the mixture at least 25%, preferably at least 50%, by weight water. Also mixtures of water and acetonitrile, there being at least 40% by weight of water in the mixture, will serve as a solvent.

EXAMPLE A

Figure 2:
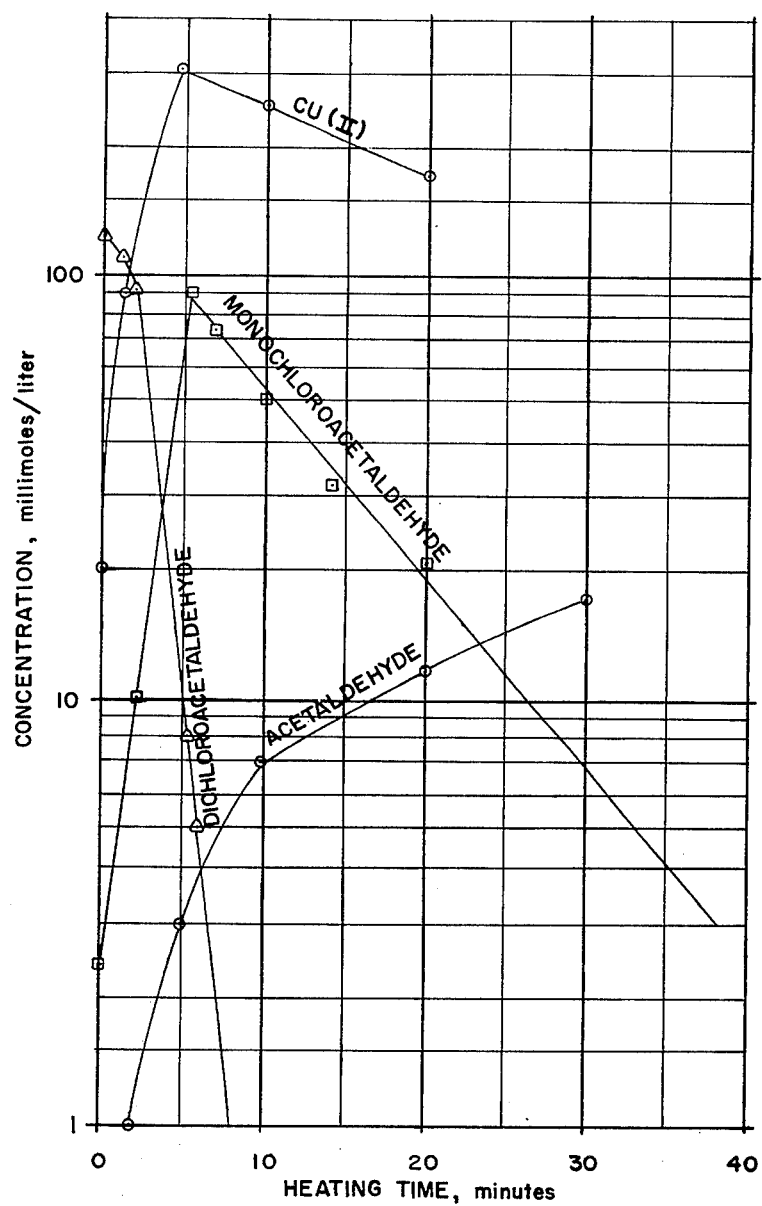
FIG. 2 is a graph illustrating the dehalogenation of dichloroacetaldehyde.

Several glass pressure tubes of about 4.5 ml. capacity were charged with an aqueous slurry containing, per liter of slurry, 1.6 moles acetic acid, 0.455 moles hydrochloric acid, 0.8 moles slurried cuprous chloride, 5 millimoles palladous chloride and 0.118 moles dichloroacetaldehyde. Each of the pressure tubes was charged with about 1.25 ml. of the slurry, with air filling the remainder of the tube, and then sealed. There was present at the beginning of each run about 25 millimoles of available oxygen. Each tube was then heated rapidly to 170° C and maintained at that temperature throughout the experiment. Each of the tubes was opened at a different time interval and the contents thereof analyzed for oxygen, cupric ions, dichloroacetaldehyde, monochloroacetaldehyde and acetaldehyde. The variation in concentration of cupric ions, dichloroacetaldehyde, monochloroacetaldehyde and acetaldehyde was then plotted against time and the results are illustrated in FIG. 2. From such FIG. 2, it may be seen that during about the first 2 minutes when there was sufficient oxygen to reoxidize any cuprous ions going into solution, the dichloroacetaldehyde did not dehalogenate to any appreciable extent. When sufficient cuprous ions did begin to accumulate in solution, a dechlorination of the dichloroacetaldehyde to monochloroacetaldehyde started taking place as indicated by the rapid increase in concentration of the latter. Thus, after 5 minutes total time, about 80% of the dichloroacetaldehyde had been dechloronated to monochloroacetaldehyde and a small portion to acetaldehyde. Simultaneously with the increase in monochloroacetaldehyde, the amount of cupric ion increased proportionately and about 310 millimoles of cupric ion had accumulated after 5 minutes. Also at the 5 minute mark, the 25 millimoles available oxygen had been depleted by oxidation of cuprous ions to cupric ions.

Of the 310 millimoles of cupric ion present after 5 minutes, 20 millimoles were present at the start, and, assuming that 100 millimoles were formed by the oxidation with the 25 millimoles oxygen (see Reaction V above), then after 5 minutes it would be theoretically predicted that 310-120 or 190 millimoles, of cupric ion, and 95 millimoles of monochloroacetaldehyde would have been formed pursuant to the following reaction:

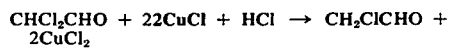

The 95 millimoles of monochloroacetaldehyde theororetically predicted closely coincides with the 90 millimoles of monochloroacetaldehyde indicated to be actually present after 5 minutes.

Still referring to FIG. 2, after about 5 minutes the amount of monochloroacetaldehyde ceased to increase and instead started decreasing rapidly, while concurrently the amount of acetaldehyde continued increasing. This indicated that the monochloroacetaldehyde was being dehalogenated to acetaldehyde. After a total of 30 minutes, about 20% of the monochloroacetaldehyde formed during the reaction was converted to acetaldehyde, the remainder having been lost through other competing reactions such as hydrolysis, aldolysis and oxidation. The significant amounts of cupric ion present after the first 5 minutes of course aids the competing oxidation reaction.

EXAMPLE B

A series of runs was made according to the procedure of Example A except that instead of the initial slurry containing 118 millimoles per liter of dichloroacetaldehyde, it instead contained 95 millimoles per liter of trichloroacetaldehyde and 20 millimoles per liter of dichloroacetaldehyde. Further, there was no available oxygen present in the initial slurry. The results of the several runs indicated that after 45 seconds about 95% of the trichloroacetaldehyde had been converted to dichloroacetaldehyde. After 3.5 minutes, no trichloroacetaldehyde remained, only about 12 millimoles of dichloroacetaldehyde remained and there had been formed 70 millimoles monochloroacetaldehyde and 5 millimoles acetaldehyde.

EXAMPLE C

Ethylene was oxidized to acetaldehyde in the apparatus shown schematically in the drawing FIG. 1. The alkene oxidation reactor 3 was operated at approximately 110° C and at a pressure of approximately 11 atmospheres absolute, while the catalyst solution reoxidation reactor 9 was operated at approximately 115° C and approximately 12 atmospheres absolute. The stripping tower 5 was operated at approximately 1.5 atmospheres absolute, and the catalyst regenerator 15 was operated at approximately 160° C and 13 atmospheres absolute. Oxygen separator pressure 10 was maintained at 11.5 atmospheres absolute.

During operation the total inventory of catalyst solution within the system was maintained at a constant level by adding water as required to compensate for losses of water in the product recovery system. The composition of the catalyst solution entering the alkene oxidation reactor 3 was approximately as follows;

| Component | Concentration |
|---|---|
| Copper moiety | 1100 millimoles/liter |
| Chloride moiety | 1700 millimoles/liter |
| Palladium moiety | 6 millimoles/liter |
| Acetic acid | 10 weight percent |
| Water | Remainder |

Per square foot of cross-section of the alkene oxidation reactor 3, there was introduced into the reactor approximately 3.5 million pounds per hour of the catalyst solution along with 11,000 pounds per hour of ethylene of approximately 99% purity. The vent gas discharge rate through conduit 19 was approximately 5,000 standard cubic feet per hour per square foot of reactor cross-section with the vent gas containing approximately 5% ethylene by volume.

Spent (i.e., chemically reduced) catalyst solution recovered from the base of the stripping tower 5 was continuously recycled to the catalyst reoxidation reactor 9 at essentially the same rate as that at which the fresh catalyst solution was introduced into the alkene oxidation reactor. Of the copper contained in the spent solution entering the reoxidation reactor 3, approximately 30% was in cuprous form. The make-up of the spent catalyst solution entering reaction 9 was as follows: cuprous chloride, 400 millimolar; cupric chloride, 700 millimolar; palladous moiety, 6 millimolar;

chloride moiety, 1700 millimolar; acetic acid, 10% by weight; acetaldehyde, 180 millimolar; chloroacetaldehydes, 45 millimolar; and with water and other by-products comprising the remainder. Per pound of spent solution entering the reoxidation reactor, approximately 0.2 standard cubic foot of air from conduit 17 was admixed, to be passed through the reoxidation reactor cocurrently with the catalyst solution for reoxidation of the contained catalyst components, e.g. copper.

From the oxygen separator 10, fixed gases, largely nitrogen and unconsumed oxygen, were vented, and the reoxidized catalyst solution was withdrawn from the base of the oxygen separator, with 99of this reoxidized solution withdrawn from the oxygen separator being passed to the alkene oxidation reactor 3 while the remaining 1% was diverted to the catalyst regeneration system. That portion of the solution which was diverted to the catalyst regeneration system was admixed with approximately 0.1 pound of 39% aqueous hydrochloric acid (through line 14) per pound of diverted catalyst solution. After passage through the catalyst regenerator 15, the resulting mixture of regenerated catalyst solution and hydrochloric acid was returned to the catalyst reoxidation reactor 9 as shown in the drawing FIG. 1.

With the process so conducted, which is in accordance with the prior art, the effluent from catalyst reoxidation reactor contains about 92 millimoles per liter of chlorinated acetaldehydes and about 130 millimoles per liter of acetaldehyde which indicates that some of the acetaldehydes entering reactor 9 have been chlorinated in reactor 9. When the total 0.2 standard cubic foot of air per pound of spent catalyst solution is divided into three equal streams such thant only one-third of the total air is injected through line 17, another one-third of the total air is injected at one-third the distance along reactor 9 (point A of FIG. 1) and the remaining one-third of the oxygen is injected at two-thirds the distance along reactor 9 (point B of FIG. 1), then the acetaldehyde content of the effluent from reactor 9 is 167 millimoles per liter while the total chlorinated acetaldehydes are present in amounts of only 53 millimoles per liter. This decrease in chlorinated acetaldehydes and increase in acetaldehyde content of the effluent when operating according to the teachings of the present invention indicates a definite improvement over the prior art.

I claim:

1. In a continuous conversion process or converting an alkene to an aldehydo alkane product, which conversion process comprises the steps of:
   a. passing said alkene through an alkene reaction zone concurrently with an acidic oxidant catalyst solution comprising a liquid containing a noble metal oxidation catalyst, cupric ions, and chloride ions, whereby said alkene is oxidized to form a reaction product comprising predominantly said aldehydo alkane product admixed with said catalyst solution in a chemically reduced condition;
   b. separating said reaction product into fractions comprising (i) an aldehydo alkane product fraction and (ii) a reduced catalyst solution fraction containing said noble metal and copper in a reduced form, including cuprous chloride in solution and as cuprous chloride crystals, and also containing hydrochloric acid, and also conaining amounts of said aldehydo alkane as well as alpha chlorinated aldehydo alkane;
   c. in an elongated plug-flow reoxidizer reoxidizing said reduced catalyst solution with a gas comprising molecular oxygen to oxidize a portion of the copper values contained therein to the cupric form; and
   d. recycling the resulting reoxidized catalyst solution to said alkene reaction zone; the improvement which comprises adding said gas comprising molecular oxygen to said catalyst reoxidation zone in a plurality of increments, each increment being added to said catalyst reoxidation zone at different points situated along the length of said zone; the first of said points being at the beginning of said zone.

2. The process of claim 1 wherein said gas comprising molecular oxygen is divided into from 2 to 10 increments.

3. The process of claim 2 wherein said increments are substantially equal.

4. The process of claim 3 wherein the said points of addition are substantially equidistant apart, there being no point of addition substantially nearer the effluent end of the said catalyst reoxidation zone than the length of the catalyst reoxidation zone divided by the number of increments.

* * * * *

UNITED STATES PATENT AND TRADEMARK OFFICE
CERTIFICATE OF CORRECTION

PATENT NO. : 4,008,279
DATED : February 15, 1977
INVENTOR(S) : Jorge A. Blay

It is certified that error appears in the above–identified patent and that said Letters Patent are hereby corrected as shown below:

In column 4, lines 55 and 56, for
"6-(bromoacetyl)-5-dimethyl-cyclohexene-4-methylcoumarin"

read -- 6-(bromoacetyl)-5-hydroxy-4-methylcoumarin --.

In column 8, line 49, for "19" read -- 9 --.

In column 10, line 2 32, for "by" read -- be --.

In column 10, line 46, for "as a" read -- has a --.

In column 11, line 52, in the equation, for "22 CuCl read -- 2 CuCl --.

In column 14, line 4, for "or" read -- for --.

In column 14, line 21, for "conaining" read -- containing --.

Signed and Sealed this

Seventeenth Day of May 1977

[SEAL]

Attest:

RUTH C. MASON
*Attesting Officer*

C. MARSHALL DANN
*Commissioner of Patents and Trademarks*